US00PP36108P2

(12) United States Plant Patent
Heuger

(10) Patent No.: US PP36,108 P2
(45) Date of Patent: Sep. 10, 2024

(54) ***HELLEBORUS* PLANT NAMED 'HLR 320'**

(50) Latin Name: ***Helleborus* x *hybridus***
Varietal Denomination: HLR 320

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/389,568

(22) Filed: Nov. 14, 2023

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Helleborus* plant named 'HLR 320', characterized by its upright to outwardly spreading and mounded plant habit; moderately vigorous to vigorous growth habit; dark green-colored leaflets with lighter green-colored venation; freely flowering habit; dark greyish purple-colored flowers; and good garden performance.

2 Drawing Sheets

Figure 1:
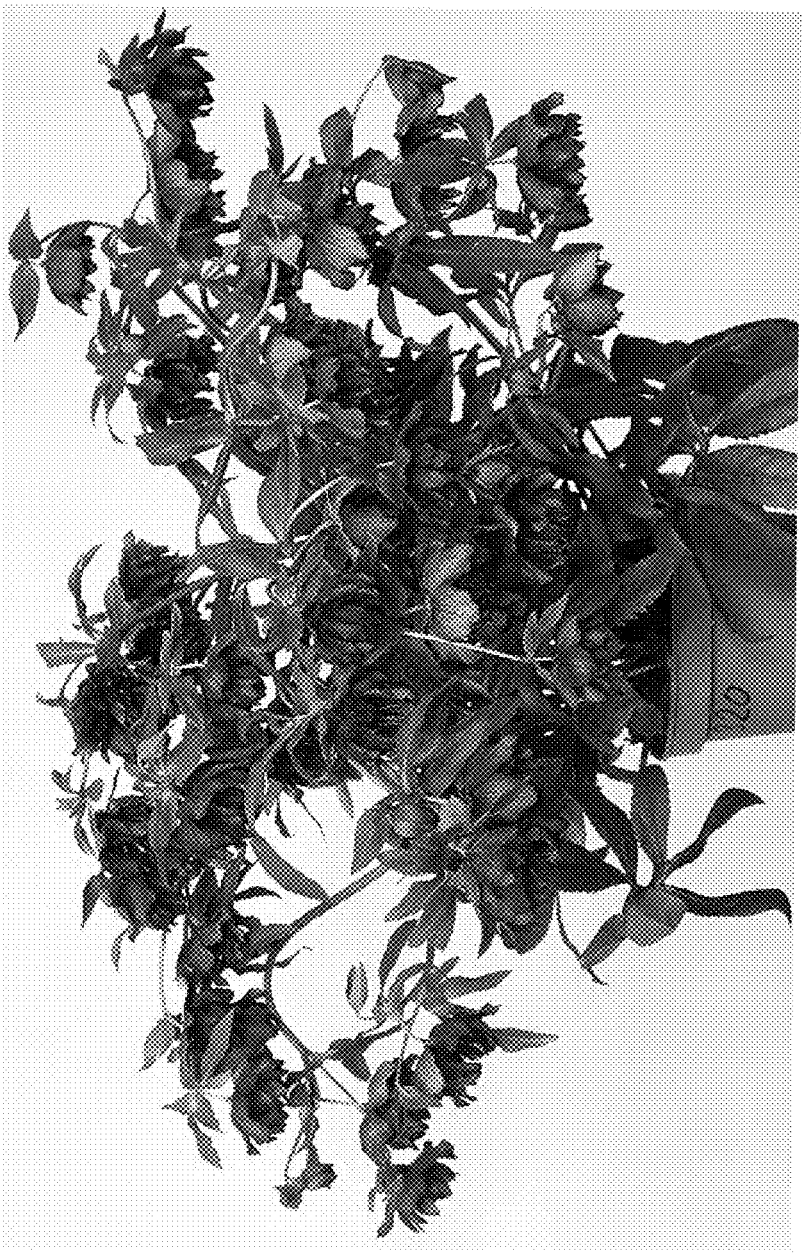

Botanical designation: *Helleborus* x *hybridus*.
Cultivar denomination: 'HLR 320'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 20, 2023, application number 2023/1375. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *hybridus* and hereinafter referred to by the name 'HLR 320'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in November, 2013 of a proprietary selection of *Helleborus* x *hybridus* identified as code number 16-23, not patented, as the female, or seed, parent and a proprietary selection of *Helleborus* x *hybridus* identified as code number 14-67, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2015.

Asexual reproduction of the new *Helleborus* plant by in vitro axillary meristem culture in a controlled environment in Glandorf, Germany since May, 2016 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HLR 320'. These characteristics in combination distinguish 'HLR 320' as a new and distinct *Helleborus* plant:

1. Upright to outwardly spreading and mounded plant habit.
2. Moderately vigorous to vigorous growth habit.
3. Dark green-colored leaflets with lighter green-colored venation.
4. Freely flowering habit.
5. Dark greyish purple-colored flowers.
6. Good garden performance.

Plants of the new *Helleborus* differ from plants of the female parent selection in the following characteristics:

1. Plants of the new *Helleborus* have larger flowers than plants of the female parent selection.
2. Flowers of plants of the new *Helleborus* are dark greyish purple in color whereas flowers of plants of the female parent selection are pink in color.

Plants of the new *Helleborus* differ from plants of the male parent selection in the following characteristics:

1. Plants of the new *Helleborus* have smaller flowers than plants of the male parent selection.
2. Flowers of plants of the new *Helleborus* are dark greyish purple in color whereas flowers of plants of the male parent selection are red in color.

Plants of the new *Helleborus* can also be compared to plants of *Helleborus* x *hybridus* 'HLR 190', disclosed in U.S. Plant Pat. No. 23,820. In side-by-side comparisons, plants of the new *Helleborus* differ primarily from plants of 'HLR 190' in the following characteristics:

1. Plants of the new *Helleborus* are more vigorous than plants of 'HLR 190'.
2. Plants of the new *Helleborus* flower earlier than plants of 'HLR 190'.
3. Flowers of plants of the new *Helleborus* are darker greyish purple in color than flowers of plants of 'HLR 190'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HLR 320' grown in a container.

Figure 2:
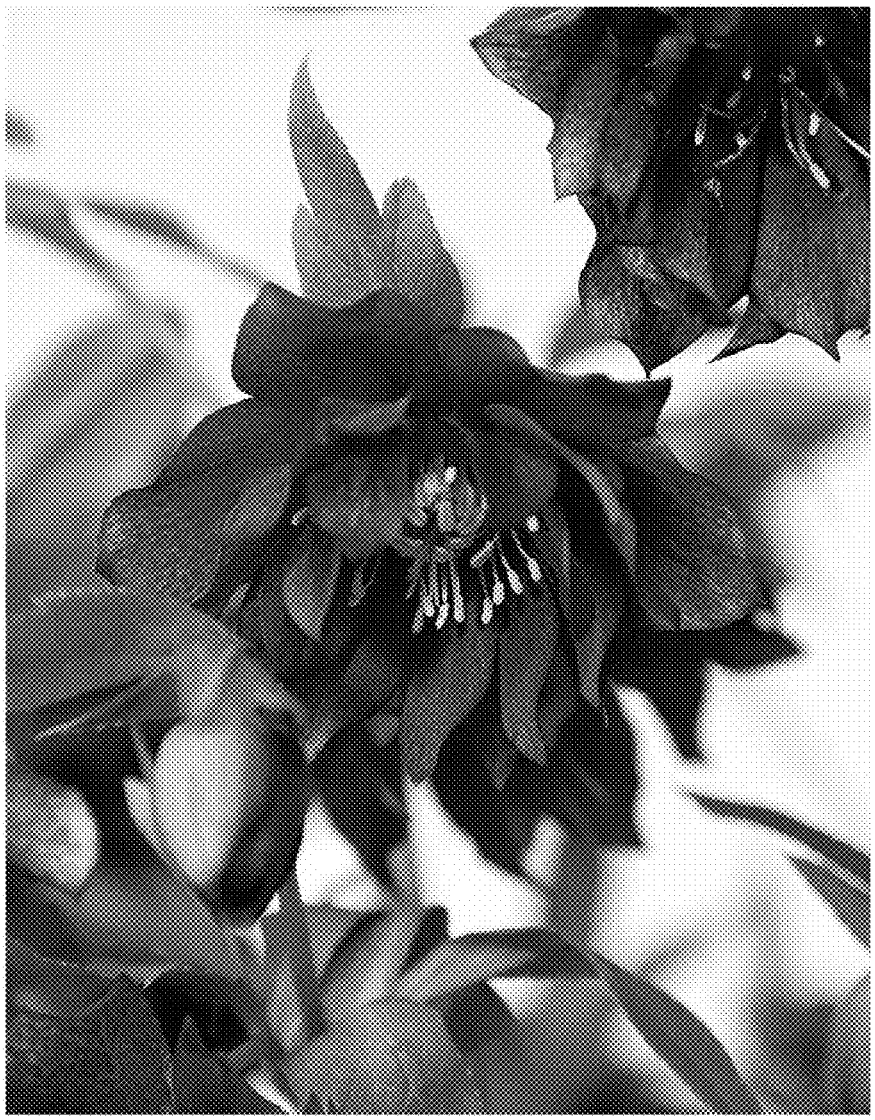

The photograph on the second sheet (FIG. 2) is a close-up view of a typical flowering plant of 'HLR 320'.

DETAILED BOTANICAL DESCRIPTION

The aforementioned photographs and following observations, measurements and values describe plants grown during the early spring in 15-cm containers in a glass-covered greenhouse in Glandorf, Germany and under cultural practices typical of commercial *Helleborus* production. During the production of the plants, day temperatures ranged from 12C to 20C and night temperatures ranged from 5C to 12C. Plants were 48 weeks old when the photographs were taken and one year old when the description was taken. In the following description, color references are made to The Royal Horticultural Society Colour Chart, 2015 Edition, except where general terms of ordinary dictionary significance are used.

Botanical classification: *Helleborus* x *hybridus* X *Helleborus* x *hybridus* 'HLR 320'.

Parentage:

*Female, or seed, parent.*—Proprietary selection of *Helleborus* x *hybridus* identified as code number 16-23, not patented.

*Male, or pollen, parent.*—Proprietary selection of *Helleborus* x *hybridus* identified as code number 14-67, not patented.

Propagation:

*Type.*—In vitro axillary meristem culture.

*Time to initiate roots, winter.*—About 55 days at temperatures about 12C.

*Time to produce a rooted young plant, winter.*—About 170 days at temperatures ranging from about 4C to 15C.

*Root description.*—Thick to thin, fleshy; typically white to brownish in color, actual color of the roots is dependent on substrate composition, water quality, fertilizer type and formulation, substrate temperature and physiological age of roots.

*Rooting habit.*—Low branching; sparse.

Plant description:

*Plant and growth habit.*—Herbaceous perennial; upright to outwardly spreading and mounding plant habit with flowers held above the foliar plane; plant shape, flattened globular; moderately vigorous to vigorous growth habit and moderate growth rate.

*Plant height, soil level to top of foliar plane.*—About 28.5 cm.

*Plant height, soil level to top of flowers.*—About 36.8 cm.

*Plant diameter* (*area of spread*).—About 60.5 cm.

Leaf description:

*Arrangement.*—Leaves arranged in a basal rosette; leaves palmately compound with typically seven leaflets per leaf.

*Leaf length.*—About 24.1 cm.

*Leaf width.*—About 24.1 cm.

*Leaflet length.*—About 14.8 cm.

*Leaflet width.*—About 5.6 cm.

*Leaf shape.*—Palmate; roughly reniform to orbicular in outline.

*Leaflet shape.*—Narrowly elliptic, narrowly obovate to oblanceolate.

*Leaflet apex.*—Acute.

*Leaflet base.*—Attenuate.

*Leaflet margin.*—Serrate; slightly coarsely undulate.

*Leaflet texture and luster, upper and lower surfaces.*—Smooth, glabrous; moderately coriaceous; slightly glossy.

*Leaflet venation pattern.*—Pinnate and reticulate.

*Leaflet color.*—Developing leaflets, upper surface: Close to 137A; towards the base, slightly tinged with close to 176B. Developing leaflets, lower surface: Close to 146A. Fully developed leaflets, upper surface: Close to 147A; towards the base, strongly tinged with close to 200B; venation, close to 144B. Fully developed leaflets, lower surface: Close to 146B; venation, close to 144B.

*Petioles.*—Length: About 19.6 cm. Diameter: About 4.5 mm by 6 mm. Strength: Strong. Texture and luster, upper and lower surfaces: Smooth, glabrous; slightly glossy. Color, upper surface: Close to 144A; slightly covered with fine dots, close to 176D and proximally, heavily covered with fine dots, close to 183A. Color, lower surface: Close to 144A; slightly covered with fine dots, close to 176C to 176D and proximally, heavily covered with fine dots, close to 183A.

Flower description:

*Flower shape and habit.*—Single rotate bowl-shaped flowers arranged in panicles; freely flowering habit with about seven flowers per inflorescence and about 90 flowers and flower buds per plant; flowers face outwardly to mostly nodding.

*Fragrance.*—None detected.

*Natural flowering season.*—Plants begin flowering about ten months after planting; plants flower naturally during the late winter in Germany.

*Flower longevity on the plant.*—About ten days; sepals persistent, other flower parts are not persistent.

*Flower buds.*—Length: About 2 cm. Diameter: About 1.3 cm. Shape: Broadly ovate. Texture and luster: Smooth, glabrous; matte. Color: Close to a blend of N77B and N186C; towards the base, tinged with close to 146C.

*Inflorescence height (including peduncle).*—About 43.1 cm.

*Inflorescence diameter.*—About 19.5 cm.

*Flower diameter.*—About 6.5 cm.

*Flower depth.*—About 4.1 cm.

*Petals.*—Petals are not transformed into nectaries. Quantity and arrangement: About 15 to 18, arranged in two whorls. Length: About 3.4 cm. Width: About 1.4 cm. Shape: Elliptic to slightly obovate; slightly concave. Apex: Acute. Base: Attenuate. Margin: Entire; coarsely undulate. Texture and luster, upper surface: Smooth, glabrous; velvety; matte. Texture and luster, lower surface: Smooth, glabrous; slightly glossy. Color: When opening, upper surface: Close to a blend of 59A and N186D; towards the base, close to 144C. When opening, lower surface: Close to a blend of N79C and 187B; towards the base, close to 144C. Fully opened, upper surface: Close to a blend of 59A and N186D; towards the margins, close to N186A; towards the base, close to 144C; venation, close to N79A; with subsequent development, color becoming closer to N77B with margins, close to N186A and at the base, close to 144B; venation, close to a blend of N77A and N186A. Fully opened, lower surface: Close to a blend of N79C and 187B; margins, close to N186A; at the base, close to 144C; venation, close to N79A; with subsequent development, color becoming closer to N186D with margins, close to N186A and at the base, close to 144B; venation, close to a blend of N77A and N186A.

*Sepals.*—Quantity and arrangement: About five, arranged in a single whorl. Length: About 3.8 cm. Width: About 2.6 cm. Shape: Broadly elliptic to broadly ovate; slightly concave. Apex: Acute. Base: Cuneate. Margin: Entire; coarsely undulate. Texture and luster, upper surface: Smooth, glabrous; matte. Texture and luster, lower surface: Smooth, glabrous; slightly glossy. Color: When opening, upper surface: Close to a blend of N186C and 187A; towards the margins and apex, close to 187D; venation, close to N186A. When opening, lower surface: Close to N77B; towards the margins and apex, close to 187C; venation, close to 187A. Fully opened, upper surface: Close to a blend of N186A and N186C; towards the margins and apex, close to 187D; venation, close to N186A; color does not change with subsequent development. Fully opened, lower surface: Close to N77B; towards the margins and apex, close to N186C; venation, close to 187B; color does not change with subsequent development.

*Flower bracts.*—Quantity per flower: Typically one or two. Length: About 7.4 cm. Width: About 7.6 cm. Shape: Narrowly ovate to reniform. Apex: Narrowly acute. Base: Cuneate. Margin: Finely serrate; slightly coarsely undulate. Color, upper surface: Close to 137A; at the base, close to 145B. Color, lower surface: Close to 146A; midvein, close to 176D.

*Peduncles.*—Length: About 31.8 cm. Diameter: About 7 mm. Aspect: About 30 degrees from vertical. Strength: Strong. Texture and luster: Smooth, glabrous; moderately glossy. Color: Close to 146C and 146D; moderately covered with fine dots and marbling, close to 176C; towards the base, more heavily covered with fine dots and marbling, close to 177B and 177C.

*Pedicels.*—Length: About 2.1 cm. Diameter: About 2 mm. Aspect: About 30 degrees from peduncle axis. Strength: Moderately strong. Texture and luster: Smooth, glabrous; moderately glossy. Color: Close to 146A.

*Reproductive organs.*—Stamens: Quantity per flower: About 60. Filament length: About 1.3 cm. Filament color: Close to 145B. Anther shape: Double and broadly reniform; basifixed. Anther size: About 17.5 mm by 3 mm. Anther color: Close to 154D. Pollen amount: Moderate. Pollen color: Close to 4D to lighter than 4D. Pistils: Quantity per flower: About five or occasionally six or seven. Pistil length: About 1.5 cm. Stigma diameter: About 0.3 mm. Stigma shape: Club-shaped. Stigma color: Close to 157A. Style length: About 1.4 cm. Style color: Close to 183D. Ovary color: Close to N144D.

*Seeds and fruits.*—To date, seed and fruit development have not been observed on plants of the new *Helleborus.*

Garden performance: Plants of the new *Helleborus* have been observed to have good garden performance and to tolerate rain, wind, high temperatures about 35C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HLR 320' as illustrated and described.

* * * * *